US005686576A

United States Patent [19]
Avraham et al.

[11] Patent Number: 5,686,576
[45] Date of Patent: Nov. 11, 1997

[54] DIFFERENTIATED MEGAKARYOCYTE LINE PRODUCING NOVEL MEGAKARYOCYTE DIFFERENTIATION FACTOR

[75] Inventors: Hava Avraham, Brighton, Mass.; Sally Cowley, London, England; Jerome Groopman, Brookline, Mass.

[73] Assignee: New England Deaconess Hospital, Boston, Mass.

[21] Appl. No.: 254,234

[22] Filed: Jun. 6, 1994

Related U.S. Application Data

[63] Continuation-in-part of Ser. No. 823,895, Jan. 22, 1992, abandoned, which is a continuation-in-part of Ser. No. 722,940, Jun. 28, 1991, abandoned.

[51] Int. Cl.$^6$ .................. C07K 14/52; A61K 38/19; C12N 5/08
[52] U.S. Cl. .................. 530/351; 435/325; 435/366; 435/372; 435/70.3; 514/2; 514/8; 424/85.1
[58] Field of Search .................. 530/350, 351; 435/240.2, 320.1, 325, 366, 372; 514/2, 8; 424/85.1

[56] References Cited

U.S. PATENT DOCUMENTS 4,894,440  1/1990  Rosenberg .................. 530/351

FOREIGN PATENT DOCUMENTS

| 0 235 113 | 9/1987 | European Pat. Off. . |
| 0 260 918 | 3/1988 | European Pat. Off. . |
| 0 354 989 | 2/1990 | European Pat. Off. . |
| WO90/12108 | 10/1990 | WIPO . |
| WO91/02001 | 2/1991 | WIPO . |

OTHER PUBLICATIONS

Meskelh R. (1995) The Oncogene Facts book Academic Press Inc. San Diego, CA 92101.
Pech et al. (1989) Mol. & Cell. Biol. vol. 9, No. 2, pp. 396–405.
Komatsu, N. et al., "Growth and Differentiation of a Human Megakaryoblastic Cell Line, CMK," *Blood*, 74(1): 42–48 (1989).
Greenberg, S.M. et al., "Relationship Between C–MYC Expression and the DNA Content of Megakaryocytic Cells," *Blood*, 76(10), Abstract No. 359 (1990).
Gewirtz, A.M. and Hoffman R., "Human Megakaryocyte Production: Cell Biology and Clinical Considerations," *Hematology/Oncology Clinics of N. America*, 4(1): 43–64 (1990).
Avanzi, G.C. et al., "Selective Growth Response to IL–3 of a Human Leukaemic Cell Line with Megakaryoblastic Features," *British J. of Haematology*, 69:359–366 (1988).

Witte, D.P. et al., "Megakaryoblastic Leukemia in an Infant," *Cancer*, 58:238–244 (1986).
Greenberg, S.M. et al., "Characterization of a New Megakaryocytic Cell Line: The Dami Cell," *Blood*, 72(6): 1968–1977 (1988).
Mladenovic J. and Anderson, S.M., "Over–Expression of C–SRC or V–SRC in Marrow Stromal Cells Stimulates Hematopoiesis by Increasing Production of GM–CSF," *Blood*, 78(10) (From Supplemental 1, Nov. 15, 1991, Abstract No. 627).
Gabbianelli, M. et al., "Pure" Human Hematopoietic Progenitors: Permissive Action of Basic Fibroblast Growth Factor, *Science*, 249:1561–1564 (1990).
Demetri, G.D. et al., "Expression of ras Oncogenes in Cultured Human Cells Alters the Transcriptional and Post-transcriptional Regulation of Cytokine Genes," *J. Clin. Invest.*, 86:1261–1269 (1990).
Tayrien, G. and Rosenberg, D., "Purification and Properties of a Megakaryocyte Stimulatory Factor Present Both in the Serum–Free Conditioned Medium of Human Embryonic Kidney Cells and in Thrombocytopenic Plasma," *J. Biol. Chem.*, 262(7) :3262–3268 (1987).
Hegyi, E. et al., "Regulation of Human Megakaryocytopoiesis: Analysis of Proliferation, Ploidy and Maturation in Liquid Cultures," *Intl. J. Cell Clon.*, 8:236–244 (1990).
Hill, R.J. and Levin, J., "Regulators of Thrombopoiesis: Their Biochemistry and Physiology," *Blood Cells*, 15:141–166 (1989).
Stenberg, P.E. and Levin, J., "Mechanisms of Platelet Production," *Blood Cells*, 15:23–47 (1989).
Hill, R.J. et al., "The Effect of Partially Purified Thrombopoietin on Guinea Pig Megakaryocyte Ploidy in vitro," *Exp. Hematol.*, 17:903–907 (1989).
Akira, F. et al., "Interleukin 6, a Possible Autocrine Growth and Differentiation Factor for the Human Megakaryocyte Cell Line, CMK," *Chem. Abstracts*, 114:590 (Apr. 15, 1991) (Abstract #114:141233n).
Mitjavila, M.T. et al., "Human Platelet Alpha Granules Contain a Nonspecific Inhibitor of Megakaryocyte Colony Formation: Its Relationship to Type β Transforming Growth Factor (TGF–β)," *J. Cell. Physiol.*, 134:93–100 (1988).
Mulligan, R.C. and Berg, P., "Expression of a Bacterial Gene in Mammalian Cells," *Science*, 209:1422–1427 (1980).

*Primary Examiner*—John Ulm
*Assistant Examiner*—Prema Mertz
*Attorney, Agent, or Firm*—Hamilton, Brook, Smith & Reynolds, P.C.

[57] ABSTRACT

Differentiated megakaryocytes produced by introducing an activated oncogene into blast-megakaryocytes is disclosed. Also disclosed are novel megakaryocyte differentiation factors and platelets obtained from the differentiated megakaryocytes.

6 Claims, 3 Drawing Sheets

5,686,576

DIFFERENTIATED MEGAKARYOCYTE LINE PRODUCING NOVEL MEGAKARYOCYTE DIFFERENTIATION FACTOR

RELATED APPLICATION

This application is a Continuation-in-Part of. U.S. Ser. No. 07/823,895, filed Jan. 22, 1992, now abandoned which is a Continuation-in-Part of U.S. Ser. No. 07/722,940 entitled "A Differentiated Megakaryocyte Line Producing Novel Differentiation Factors" by Jerome E. Groopman, Hava Avraham and Sally Cowley, filed Jun. 28, 1991 now abandoned. The teachings of the cited applications are incorporated herein by reference.

GOVERNMENT SUPPORT

Work described herein was supported in part by the National Institute of Health. The United States government has rights in the subject invention.

BACKGROUND OF THE INVENTION

Blood platelets are required for the maintenance of normal hemostasis. Platelets initiate blood clot formation and release growth factors that speed the process of wound healing and may serve other functions.

Platelets are the terminal differentiation product of megakaryocytes, which in turn originate from pluripotent stem cells of the bone marrow. The maturation and differentiation processes that begin with pluripotent stem cells and end with blood platelets are complex and incompletely understood. However, it is thought that humoral factors influence different cellular steps in megakaryocyte development.

Thrombocytopenia (i.e., depressed levels of platelets) can result from genetic problems affecting megakaryocytopoiesis in an individual. It can also result from therapies for cancer (e.g., chemotherapy and radiation) and bone marrow transplantation.

Thrombocytopenia is currently treated mainly with platelet transfusions. However, it is expensive to obtain platelets from human donors. In addition, platelets for transfusions have a relatively short shelf-life and their use can expose the patient to dangerous viruses (e.g., HIV and hepatitis).

A greater understanding of megakaryocytopoiesis, as well as isolation and identification of humoral factors which promote megakaryocytopoiesis are greatly needed.

SUMMARY OF THE INVENTION

The present invention relates to Applicants' finding that blast-megakaryocytes, which have been transfected with an activated oncogene, differentiate into mature megakaryocytes. Thus, the invention comprises in one embodiment, a method of producing terminally differentiated megakaryocytes through the introduction of a gene encoding an activated oncogene into blast-megakaryocytes, which subsequently become more differentiated. Preferred blast-megakaryocytes are CMK cells.

In the present method, blast-megakaryocytes are maintained under conditions appropriate for their growth as non-terminally differentiated cells. A gene encoding an activated oncogene is then introduced into these megakaryocytes, thereby producing megakaryocytes containing an activated oncogene. The resulting activated, oncogene containing cells are then cultured under conditions sufficient for their growth and differentiation. A number of these cells become polyploid and terminally differentiate. The invention also particularly relates to differentiated megakaryocytes produced by the method and uses therefor. Other aspects of the present invention relate to platelets produced by the method of the subject invention and uses therefor.

A further aspect of the present invention relates to a novel differentiation factor produced by the differentiated megakaryocytes of the subject invention and uses therefor. This megakaryocyte differentiation factor (MDF) is present in the supernatant of oncogene activated, differentiated megakaryocytes. When megakaryocyte cells are cultured in the presence of the MDF produced by the differentiated megakaryocytes, there is a marked increase in proliferation of megakaryocyte cells as well as increase in ploidy number. This differentiation factor is heat sensitive and protease sensitive, suggesting that this factor is proteinaceous in nature. In addition, this MDF does not have any detectable GM-CSF, IL-3, IL-6 or IL-1B activity, making it clear that it is not one of these previously identified lymphokines or cytokines.

DETAILED DESCRIPTION OF THE INVENTION

Figure 1:
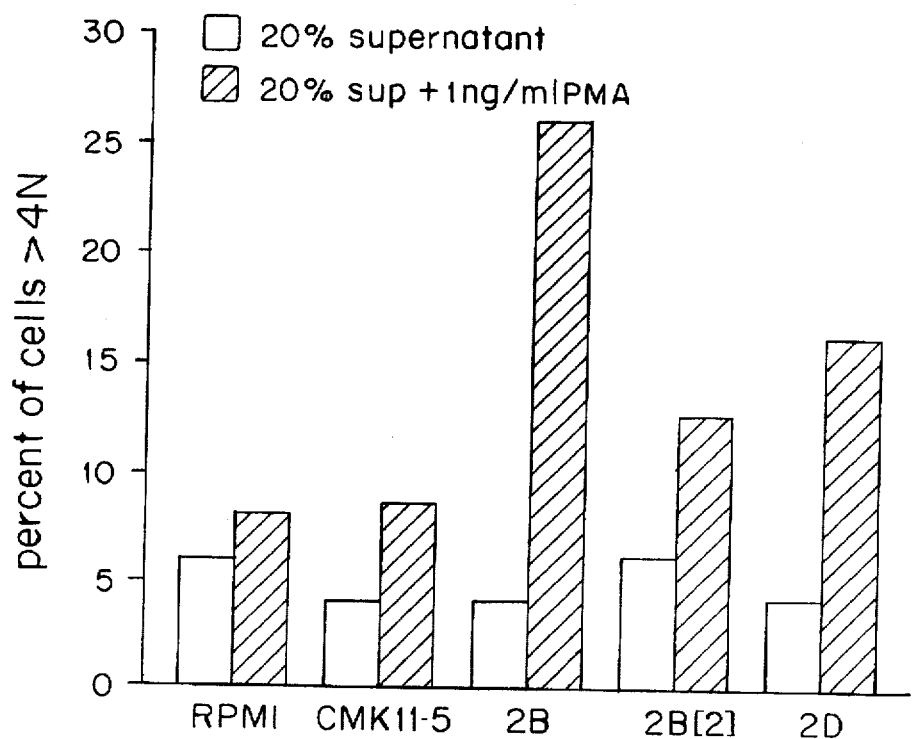
FIG. 1 is a graphic representation of the effect of ras-transfected megakaryocyte supernatant on CMK11-5 ploidy.

The present invention relates to Applicants' finding that blast-megakaryocytes transfected with an activated oncogene differentiate into mature megakaryocytes capable of producing a soluble factor which mediates growth and differentiation of megakaryocytes. The invention comprises, in one embodiment, a method of producing differentiated megakaryocytes by introducing a gene encoding an activated oncogene into blast-megakaryocytes or other appropriate precursor cell.

A unique feature of megakaryocytes is their ploidy number, which is characterized by a geometric progression of DNA levels. "Ploidy number" is a term used to describe the number of copies of chromosomes within a cell. An increase in ploidy number indicates that there are more than the usual number of copies of chromosomal DNA in the cell nucleus, a distinctive characteristic of differentiated megakaryocytes. Thus, the measure of ploidy number of megakaryocytes is an indication of the maturity of the cell.

Blast-megakaryocytes, like mature megakaryocytes, also express platelet specific phenotypic markers. Blast-megakaryocytes mature from megakaryocyte progenitor cells (i.e., the burst forming unit—megakaryocyte (BFU-M) and the colony forming unit—megakaryocyte (CFU-M)), proceeding through a phase characterized by mitotic division of progenitor cells followed by a wave of nuclear endoreplication, occurring in a nonproliferating cell.

Blast-megakaryocytes are morphologically recognizable by size, which ranges from about 15 to 40 μm, the presence of lobulated nuclei, and ploidy number, which ranges from 2N to 8N. In addition they may contain a few cytoplasmic organelles (e.g., mitochondria, golgi apparatus, endoplasmic reticulum). Blast-megakaryocytes, like mature megakaryocytes, also express platelet specific phenotypic markers, such as adhesion structures and granule content, and lack cytoplasmic organelles, such as mitochrondria and endoplasmic reticulum.

For purposes of the present method of producing differentiated megakaryocytes and their products, preferred blast-megakaryocytes are CMK cells. (Komatsu, N. et al., *Blood* 74:42–48 (1989)). However, examples of other blast-megakaryocyte cell lines useful in the present invention are DAMI (Greenberg, S. M. et al., *Blood* 72:1968–1977 (1988)) and CHRF (Wilte, D. P. et al., *Cancer* 58:238 (1986)).

A preferred activated oncogene to introduce into a blast-megakaryocyte is the cytoplasmic oncogene, ras, which has been implicated in transformation in vitro and tumorigenesis in vivo. However, other cytoplasmic oncogenes (e.g., avian myb) may also be useful in the subject invention. Cytoplasmic oncogenes, in contrast to nuclear oncogenes, exert their effect in the cell's cytoplasm.

A gene encoding an activated cytoplasmic oncogene such as ras can be introduced into a blast-megakaryocyte using known genetic engineering transfer techniques. For example, the gene can be introduced by incubating megakaryocytes with a calcium phosphate precipitate of DNA, electroporation, direct intracellular micro-injection, infection of cells with modified vectors (e.g., retroviral vectors) or fusion of cells with other cells, sperm or with liposomes, which contain the oncogene. Alternatively, an inactivated form of the gene can be introduced into blast-megakaryocytes and then can be activated in vivo (e.g., chemically or by amplifying the number of copies).

Example 1 sets forth in detail a method of introducing the activated ras oncogene into blast-megakaryocytes. Blast-megakaryocytes were maintained under conditions appropriate for their growth as non-terminally differentiated cells. Two plasmids, one containing a gene encoding an activated oncogene and the other containing a gene encoding a selectable marker were then co-transfected into the megakaryocytes by electroporation. Transfected cultures were maintained for three weeks in selective medium, which was changed every three days. Resistant colonies were picked by the limiting dilution method.

The differentiated megakaryocytes produced by introducing a gene encoding an activated oncogene into blast-megakaryocytes differ from non-oncogene containing blast-megakaryocytes in the following respects: 1) they are larger in size, (e.g., their size ranges from 60 to 120 μm; 2) they have increased ploidy values (e.g., ploidy ranging from 16N–32N); and 3) they contain many cytoplasmic organelles (e.g., mitochondria, golgi apparatus and endoplasmic reticulum).

In addition, some of these differentiated megakaryocytes produce a novel differentiation factor referred to herein as megakaryocyte differentiation factor (MDF). In particular, supernatant from H-ras transfected CMK11-5 cells and megakaryocytic cell clones, 2B and 2D, (subclones of CMK11-5 transfected cells) demonstrate a significant effect on megakaryocyte differentiation in vitro. One megakaryocytic clone producing differentiation factors (ras meg A, herein referred to as 2D) was deposited (Jun. 27, 1991) under terms of the Budapest Treaty at the American Type Culture Collection (Rockville, Md.) under ATCC accession number CRL 10817.

Growth factor dependent human and murine megakaryocytic cell lines (e.g., CMK11-5, CMK-G; and SO) are used as assay targets in the studies of the MDF produced by the H-ras transfected megakaryocytes. These cell lines proliferate in response to cytokines, such as GM-CSF, interleukin-3, or erythropoietin.

Initial studies were performed using primary human bone marrow megakaryocytes (CMK11-5) as target megakaryocytes. These bone marrow megakaryocytes were cultured with supernatants from the differentiated megakaryocytes transfected with H-ras. Importantly, culturing CMK11-5 cells in the presence of differentiated megakaryocyte cell supernatants resulted in an increase in megakaryocyte ploidy number. These assays were done with crude, unconcentrated unfractionated supernatant, as well as with crude, unconcentrated, unfractionated supernatant supplemented with PMA. (See FIG. 1).

Figure 2A:
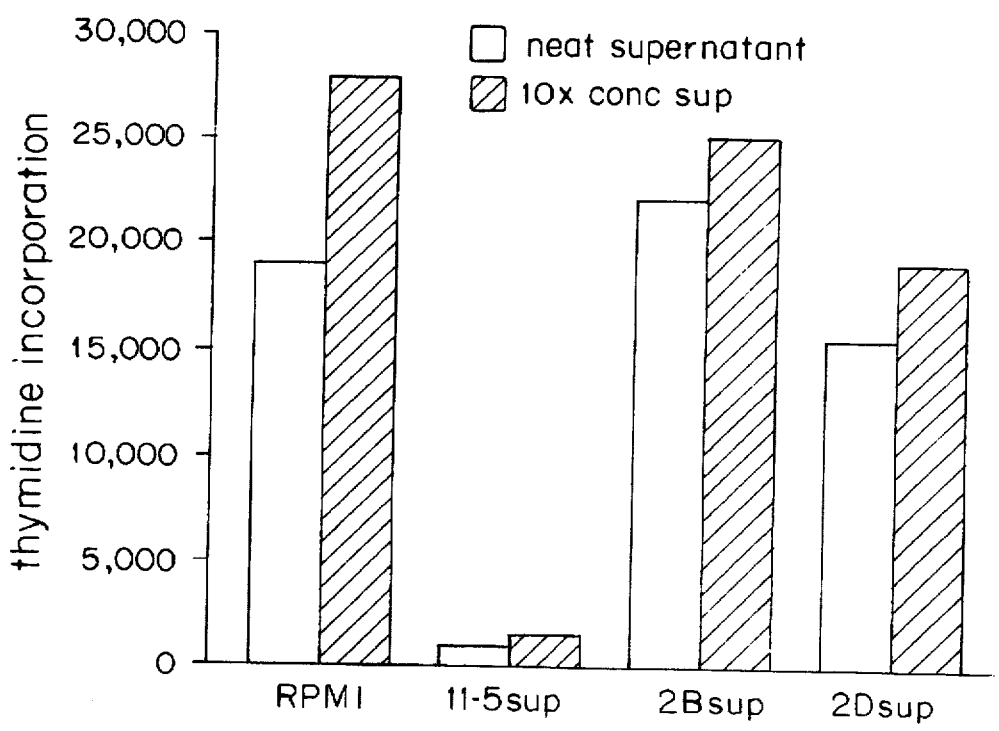
FIG. 2A is a graphic representation of the effect of ras-transfected megakaryocyte supernatant on growth factor-dependent cell line UT7.
Figure 2B:
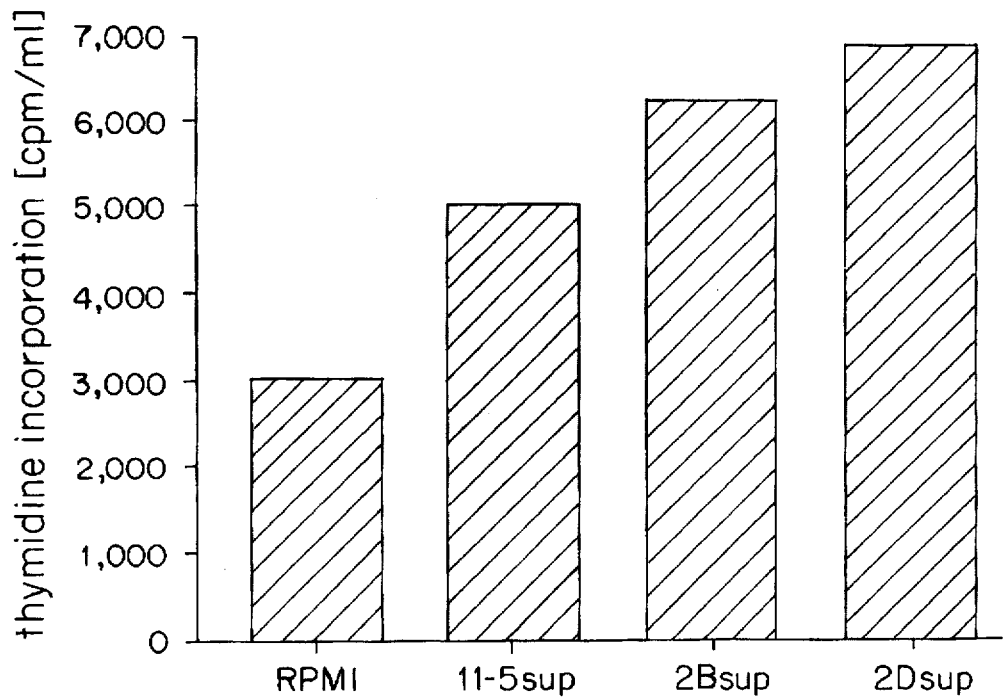
FIG. 2B is a graphic representation of the effect of ras-transfected megakaryocyte supernatant on growth factor-dependent cell line MO7.

As described in Example 2, supernatants from the H-ras transfected megakaryocytes induced a marked increase in tritiated thymidine incorporation in parent (unaltered) CMK and growth factor dependent UT7 and M07 cells. (See FIGS. 2A and 2B).

Characterization of this activity revealed that it was heat sensitive, that is, the activity was destroyed by heating at 56° C. for 30 minutes. Treatment of this supernatant material with proteinase-K also destroyed MDF activity indicating that MDF is protenaceous in nature.

Figure 3:
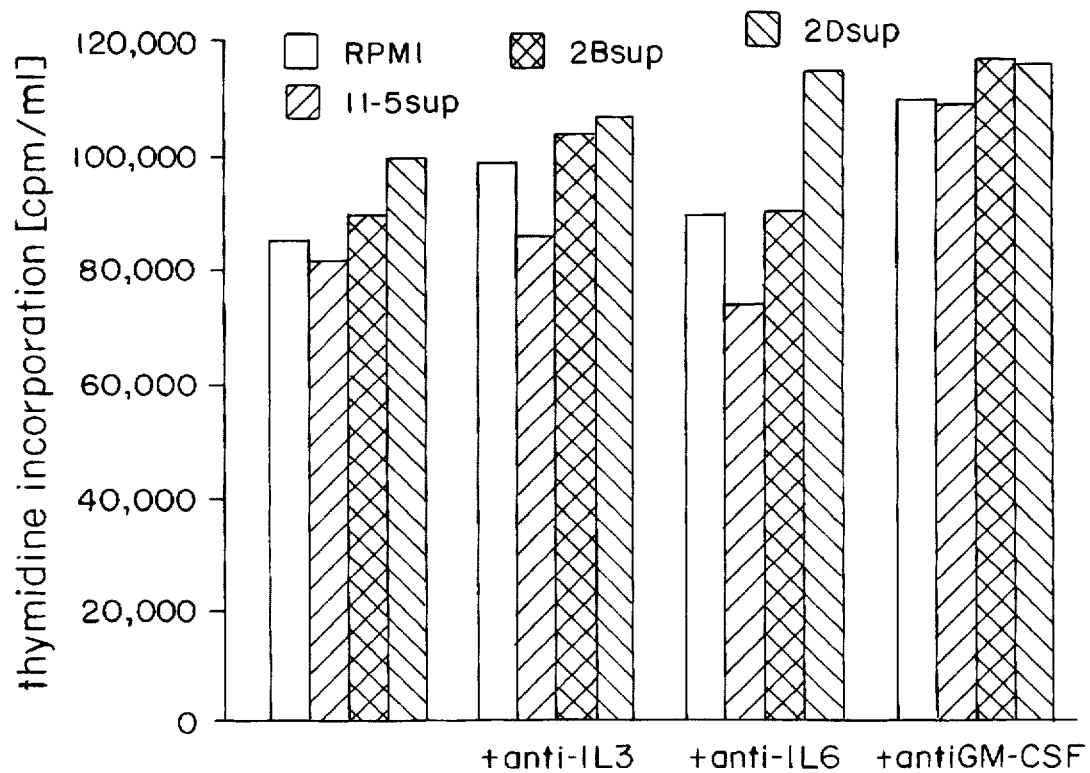
FIG. 3 is a graphic representation of the effect of blocking ras-transfected megakaryocyte supernatant activity with anti-cytokine antibodies.

To verify whether the MDF activity observed was due to a known cytokine, neutralization experiments using specific antibodies for IL-3, IL-6, GM-CSF and IL-1B were performed. These experiments revealed that the MDF activity was not neutralized by these antibodies, singly or in combination. These results indicate that the activity from the transfected megakaryocyte supernatants is a novel growth factor. (See FIG. 3).

To examine whether the MDF activity alone, or in combination, with IL-3, IL-6 and GM-CSF could act synergistically, ploidy assays were performed after 6 days on bone marrow isolated megakaryocytes. These experiments revealed that marrow megakaryocytes isolated by immunomagnetic beads coated with anti-GpIIb/IIIa antibody were predominantly 2N, with a small proportion containing 4N ploidy. Following treatment with 2B supernatant, an increase in 4N (8.3%) and 8N (2.7%) cells as compared with cells cultured in RPMI alone, was observed (See Table I).

In combination with IL-6, the 8N population was increased in the presence of 2B or 2D. These results demonstrate that the factors released by oncogene-activated megakaryocyte cells have an identifiable effect on megakaryocyte ploidy (indicating megakaryocyte differentiation) and can act synergistically with IL-6.

TABLE I

The Effects of ras Transfected Megakaryocyte Supernatant on Ploidy of Isolated Megakaryocytes

| | Experiment A | | |
|---|---|---|---|
| | % 2N | 4N | 8 |
| RPMI | 84.6 | 6.3 | — |
| CMK11-5 sup | 76.5 | 8.9 | 1.7 |
| 2B sup | 79.0 | 8.3 | 2.7 |
| 2D sup | 79.0 | 6.8 | 1.1 |

TABLE I-continued

The Effects of ras Transfected Megakaryocyte Supernatant on Ploidy of Isolated Megakaryocytes Experiment B

| +IL-6 | % 2N | 4N | 8N |
|---|---|---|---|
| RPMI | 76.0 | 8.9 | 0.9 |
| CMK11-5 sup | 72.9 | 11.5 | 4.2 |
| 2B sup | 74.1 | 10.8 | 3.2 |
| 2D sup | 79.3 | 9.2 | 2.7 |

Supernatants from ras transfected, differentiated megakaryocytes were also assessed for their effects on megakaryocyte colony formation, as described in Example 3. Culturing in the presence of supernatants from the 2B and 2D clones resulted in significant increases in the formation of total hematopoietic cell colonies, as well as increases in megakaryocyte colony forming units (CFU-meg) and single megakaryocyte cells. (See FIG. 4).

In addition to testing MDF on CMK cells, SO cells were also tested. The SO cell line was derived from a megakaryoblastic leukemia patient, and are less mature than CMK cells based on CD34, gpIb and gpIIb/IIIa surface staining. Results of these studies are shown in Tables II and III. These results also demonstrate megakaryocyte differentiation effect of MDF on less mature megakaryocytes.

column, Pharmacia, Inc.), as described in Example 4. After fractionation, every alternate fraction was recovered, 10% fetal bovine serum (FBS) was added to each fraction and filtered through a 0.2mm filter unit and assayed in the single cell assay as described in Example 2. The results, as shown in Example 4, indicate that MDF activity peaked in fraction 8. The active fractions were pooled and the protein concentration of the pooled fractions was determined and tested as described in Example 2.

Further purification can proceed, for example, as follows. After the anion exchange column, pooled fractions containing megakaryocyte stimulating activity are loaded on a Superdex 75 column (Pharmacia Inc.). After fractionation, every alternate fraction is recovered, treated with 10% FBS and filtered through a 0.2 mm filter unit. These fractions are then assayed in the single cell assay. The active fractions are again pooled and protein concentration determined.

The pooled fractions containing MDF activity after the anion exchange and gel filtration columns are then loaded on a HPLC reverse phase column, which separates proteins on the basis of hydrophobicity. After fractionation, every alternate fraction is treated with 10% FBS, filtered and assayed in the single cell assay. The active fractions are again pooled and lyophilized, thus ready for peptide sequencing usually standard laboratory procedures.

Additional steps needed to characterize the MDF activity can include, for example, the determination of the isoelectric point by Mono-P (Pharmacia, Inc.) column isoelectric

TABLE II

Effect of 10x Concentrated 2B/2D Supernatant on Maturation

| Conditions | [$^3$H] cpm | Cell No. | GpIP | GpIIb/IIIa |
|---|---|---|---|---|
| SO - control | 7688 ± 768 | 18 × 10$^4$ ± 3 × 10$^4$ | 4.8% ± 3% | 75% ± 6% |
| + IL-6 | 13180 ± 606 | 22 × 10$^4$ ± 4 × 10$^4$ | 7.3% ± 2% | 82% ± 5% |
| + PMA | 5320 ± 478 | 06 × 10$^4$ ± 2 × 10$^4$ | 25.2% ± 5%* | 100% ± 6% |
| 10x Sup CMK11-5-25% | 5560 ± 570 | 15 × 10$^4$ ± 3 × 10$^4$ | 9.1% ± 2%* | 83% ± 3% |
| 10x Sup 2B-25% | 5532 ± 534 | 13 × 10$^4$ ± 4 × 10$^4$ | 9.3% ± 1%* | 75.6% ± 6% |
| 10x Sup 2D-25% | 5342 ± 556 | 13 × 10$^4$ ± 3.5 × 10$^4$ | 12.4% ± 3%* | 91.2% ± 5% |

*Significantly elevated in the cultures of CMK-G treated with supernatant 2B/2D or PMA compared to CMG-G alone (p < 0.05).

TABLE III

Ploidy Analysis

| | 2N | 4N | ≧8N |
|---|---|---|---|
| SO Control | 62.5 ± 1.1 | 11.9 ± 1.3 | 1.5 ± 0.6 |
| +IL-6 (10 ng/ml) | 64.5 ± 0.8 | 13.4 ± 2.3 | 3.86 ± 1.1* |
| +PMA (10 ng/ml) | 46.5 ± 1.2 | 15.2 ± 3.3* | 9.02 ± 3.3* |
| 25% Concentrated CMK11-5 Sup | 54.9 ± 1.4 | 12.4 ± 0.9* | 6.7 ± 1.3* |
| 2B Sup | 54.6 ± 2.2 | 17.5 ± 1.3* | 7.5 ± 1.3* |
| 2D Sup | 55.7 ± 0.8 | 17.7 ± 2.2* | 6.5 ± 1.11* |

*Results are give as = SEM of three independent experiments. Significantly elevated in the cultures of CMK-G treated with supernatant or PMA compared to CMK-G alone (p < 0.05)

MDF from clone 2D supernatant (conditioned media) was partially purified as follows. The conditioned medium was concentrated on an Amicon concentration unit, either 10 fold, or 15 fold, and the protein concentration was determined by the commercially available Biorad Assay kit (Coomassie blue).

10 ml of concentrated conditioned medium was fractionated on an anion exchange column (Resource Q, 1 ml focusing, and the determination of carbohydrate content by wheat germ agglutium or concavalin-A column. These procedures are well-known to those of skill in the art.

Alternatively, a gene encoding a megakaryocyte differentiation factor can be isolated from a cDNA library made, for example, from the total RNA of a megakaryocyte which contains an activated oncogene, using known techniques. Once isolated, the gene encoding a megakaryocyte differentiation factor can be cloned into an expression vector, which can be used to express the MDF in vitro or in vivo.

In addition to producing differentiation factors, the differentiated megakaryocytes of the subject invention can be useful for producing platelets, both in vitro and in vivo. A therapeutically effective amount of either platelets produced in vitro from differentiated megakaryocytes or differentiation factors isolated from differentiated megakaryocytes can be administered to a vertebrate (e.g., a human) with a platelet-associated bleeding disorder (e.g., thrombocytopenia) to treat the bleeding disorder. A therapeutically effective amount is that amount sufficient to significantly reduce or eliminate the symptoms, or effects of the platelet disorder.

The number of platelets or quantity of differentiation factors to be administered to a vertebrate for therapeutic effectiveness can be determined on an individual basis and will be based, at least in part, on considerations of the individual's size, the severity of the symptoms being treated, and the results sought. A therapeutically effective amount can be determined by one of ordinary skill in the art using no more than routine experimentation. Administration of platelets or a megakaryocyte differentiation factor can be by any route appropriate for the condition being treated, but typically platelets will be administered parenterally (e.g., via intravenous (IV) or intra-arterial (IA) injection); and MDF will be administered subcutaneously or parenterally.

Furthermore, the MDF of the present invention can be used to stimulate in vitro production of differentiated megakaryocytes. These megakaryocytes can be useful in screening assays for, e.g., cytokine or lymphokine activity or in screening procedures to test novel factors for platelet producing activity.

The present invention will now be illustrated by the following Examples, which are not to be seen as limiting in any way.

EXAMPLE 1

Transfection of CMK Cells With Activated ras

Cell Culture

CMK11-5 cells (approximately 90–95% 2N) were grown in RPMI 1640 medium containing 5% platelet poor plasma, L-glutamine, penicillin and streptomycin as described in Mitjavila, M. T. et al., *J. Cell. Physiol.*, 734:93(1986).

Plasmids

Two plasmids were used for co-transfection experiments: pSV2neo (Mulligan, R. C., et al., *Science*, 19:1422 (1980)) and pSVET24 (Seeburg, P. H. et al., *Nature*, 312:71 (1984)).

Transfections

Transfections were performed by electroporation, essentially as described in Andreason and Evans *Bio Techniques*, 6:650 (1988). For cotransfections and selection, 5 μg of plasmid DNA pSVET 24 were mixed with 0.5 μg of pSV2neo. Twenty-four hours after transfection, the cells were plated onto 100 mm dishes, and gentamicin (G418; Gibco Laboratories) was added to 400 μg/ml. Cultures were maintained for three weeks with the medium being changed every three days. At the end of this period, resistant colonies were picked by the limiting dilution method. The clones were expanded and analyzed further for their morphology and for the presence of platelet specific markers.

EXAMPLE 2

Testing Supernatants From ras Transfected CMK11-5 Cells on CMK Cells

Spectrophotometric measurement of DNA content of CMK cells:

CMK cells (approximately 90–95% 2N) were seeded at $2\times10^5$ cells and fed again after two days. Cells were harvested after 5 days and the nuclei were isolated, stained with propidium iodide, and analyzed on a Becton Dickinson FACS Analyzer (Mountain View, Calif.) as previously described (Greenberg, S. M. et al., *Blood*, 72:1968 (1988)). Freshly prepared lymphocytes were used to mark the position of the 2N cells.

Proliferation assays:

Cell proliferation and viability was assessed by $^3$[H] thymidine incorporation and by trypan blue exclusion (0.4% trypan blue stain in 0.85% saline, Gibco Laboratories). Supernatants were added in a volume of 50 μl in 96-well flat-bottom tissue culture plates (Costar, Cambridge, Mass.) where CMK11-5 cells were seeded at $2\times10^4$ cells in the appropriate growth medium containing either 1% platelet poor plasma or 1% fetal calf serum (4FCS) in a final volume of 100 μl. For $^3$[H] thymidine incorporation assays, cells were seeded at time zero (50 μl volume) and the plates were incubated at 37° C. in a humidified atmosphere of 5.5% $CO_2$ for 48 hours. Cells were pulsed with 0.5 Ci per well of $^3$[H] thymidine (25 A/retool, NEN, Boston) and incubated for an additional five hours. Samples were harvested onto glass fiber filters and counted by liquid scintillation spectrometry.

EXAMPLE 3

Colony Forming Assay

Murine bone marrow cells (BM) were cultured under standard conditions in the presence of Murine IL-3 (control), RPMI media with and without platelet poor plasma (PPP) or PMA, or the 2B and 2D clone supernatants, with or without cytokine supplements.

Figure 4:
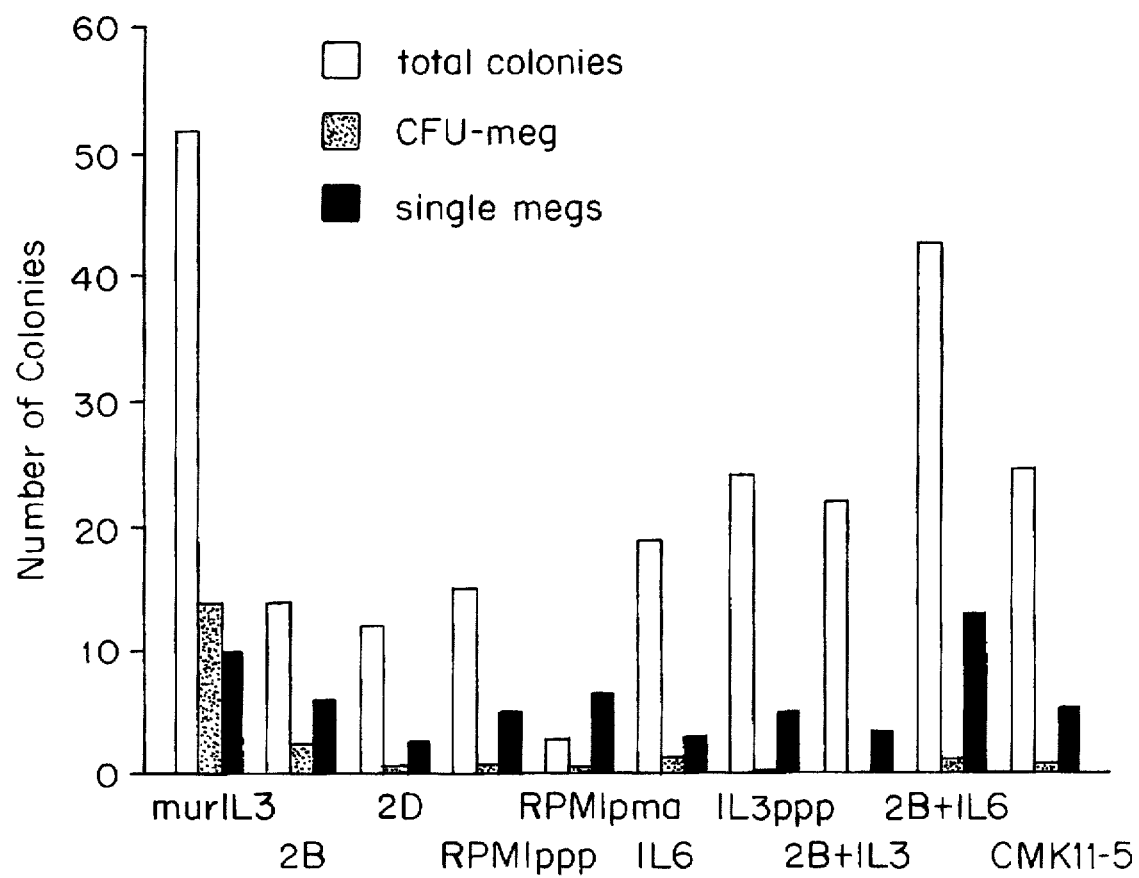
FIG. 4 is a graphic representation of the effect of ras-transfected megakaryocyte supernatant on colony formation by murine bone marrow (MB) cells.

After incubation for approximately 14 days, total colonies formed, CFU-meg colonies and single megakaryocyte cells were tabulated. The results, as shown in FIG. 4, indicate that the 2B and 2D supernatants cause significant increases in total colonies and single megakaryocytes formed, with or without supplemented cytokines.

EXAMPLE 4

Partial Purification of MDF

MDF was partially purified using an anion exchange column. The anion exchange column material was Resource Q, obtained from Pharmacia, Inc. The starting buffer was 0.02 m Tris-HCl, pH 8.0 and the gradient buffer contained 0.3 m NaCl starting concentration. The sample was 10 mls of 10×concentrated 2D conditioned medium, loaded in four consecutive applications. After fractionation, 500 μl aliquots of alternate fractions were mixed with 50 μl FBS, filtered and a 100 μl aliquot of each fraction was assayed by single cell assay. The results are shown in Table IV.

TABLE IV

| Fraction Number | Megakaryocytes/5 × 10⁴ cells plated (Avg ± SEM) |
|---|---|
| 2 | 16 ± 1.0 |
| 4 | 17 ± 1.0 |
| 6 | 17 ± 1.4 |
| 8 | 22 ± 1.0 |
| 10 | 16.0 ± 0.5 |
| 12 | 13.0 ± 1.0 |
| 14 | 17.0 ± 0.0 |
| 16 | 11.0 ± 0.0 |
| 18 | 14 ± 4.5 |
| 20 | 9 ± 0.0 |
| 22 | 11 ± 0 |
| 24 | 18 ± 1.0 |
| 26 | 15 ± 0 |
| 28 | 11 ± 0 |
| 30 | 11 ± 0 |
| Unfractionated 2D CM | 33 ± 1 |
| FCS Control | 15.3 ± 1.5 |

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An isolated extracellular megakaryocyte differentiation factor which mediates differentiation in megakaryocytic cells not transfected with an activated oncogene, wherein said factor has the following characteristics:
   a) is produced and secreted by a differentiated human megakaryocytic cell transfected with an activated ras gene;
   b) is soluble, heat-sensitive and protcase sensitive;
   c) has no detectable GM-CSF, IL-3, IL-1B, or IL-6 activity; and
   d) induces an increase in ploidy number in megakaryocytes cultured in the presence of said factor.

2. A composition comprising an amount of the isolated megakaryocyte differentiation factor of claim 1 effective to stimulate platelet production and a physiologically compatible carrier.

3. The isolated megakaryocyte differentiation factor of claim 1 produced and secreted by the megakaryocytic cell line ATCC No. CRL 10817.

4. An isolated megakaryocyte differentiation factor produced and secreted by the megakaryocytic cell line ATCC No. CRL 10817.

5. The megakaryocytic cell line ATCC No. CRL 10817.

6. An isolated megakaryocyte differentiation factor which mediates differentiation in megakaryocytic cells not transfected with an activated oncogene, wherein said factor has the following characteristics:
   a) is present in supernatant obtained from a differentiated human megakaryocytic cell transfected with an activated ras gene;
   b) is soluble, heat-sensitive and protease-sensitive; and
   c) has no detectable GM-CSF, IL-3, IL-1B, or IL-6 activity; and
   d) induces an increase in ploidy number in megakaryocytes cultured in the presence of said factor.

* * * * *